United States Patent
Gliner et al.

(10) Patent No.: US 12,204,106 B2
(45) Date of Patent: Jan. 21, 2025

(54) PRESENTING VISUAL AND THERMAL IMAGES IN A HEADSET DURING PHACOEMULSIFICATION

(71) Applicant: JOHNSON & JOHNSON SURGICAL VISION, INC., Irvine, CA (US)

(72) Inventors: Vadim Gliner, Haifa (IL); Assaf Govari, Haifa (IL)

(73) Assignee: Johnson & Johnson Surgical Vision, Inc., Irvine, CA (US)

(*) Notice: Subject to any disclaimer, the term of this patent is extended or adjusted under 35 U.S.C. 154(b) by 199 days.

(21) Appl. No.: 16/998,522

(22) Filed: Aug. 20, 2020

(65) Prior Publication Data

US 2022/0057635 A1 Feb. 24, 2022

(51) Int. Cl.
G02B 27/01 (2006.01)
A61F 9/007 (2006.01)

(52) U.S. Cl.
CPC ...... *G02B 27/0172* (2013.01); *A61F 9/00745* (2013.01); *G02B 2027/0138* (2013.01); *G02B 2027/014* (2013.01); *G02B 2027/0141* (2013.01)

(58) Field of Classification Search
CPC ........ G02B 27/0172; G02B 2027/0138; G02B 2027/014; G02B 2027/0141; A61F 9/00745; A61B 2017/00203; A61B 3/0058; A61B 2090/365; A61B 2090/371; A61B 2090/372; A61B 2090/502; A61B 90/36; A61B 90/37

See application file for complete search history.

(56) References Cited

U.S. PATENT DOCUMENTS

| | | | |
|---|---|---|---|
| 10,639,104 B1* | 5/2020 | Barral | A61B 34/20 |
| 2006/0048286 A1* | 3/2006 | Donato | G08B 13/19634 348/E7.086 |
| 2009/0024023 A1* | 1/2009 | Welches | A61B 18/201 600/549 |
| 2012/0022546 A1 | 1/2012 | Hubschman et al. | |
| 2012/0155778 A1* | 6/2012 | Buchmueller | G06F 16/583 382/209 |

(Continued)

FOREIGN PATENT DOCUMENTS

| | | |
|---|---|---|
| JP | 2017079904 A | 5/2017 |
| WO | 2013112554 A1 | 8/2013 |

(Continued)

*Primary Examiner* — Ricardo Osorio (57) ABSTRACT

A surgical imaging system, including a first imaging device configured to generate a real-time visual image of a first field of view of a patient, and a second imaging device configured to generate a real-time thermal image of the first field of view. The system also includes a retaining structure, configured to be positioned in proximity to an eye of an operator, and a semitransparent screen configured to be mounted on the structure. The system additionally includes a processor configured to receive the images, and upon receiving an indication from the operator, to present, on the screen, the real-time visual image, or the real-time thermal image or the real-time thermal image overlaid on the real-time visual image, focused to a point in proximity to a near point of the eye while the operator can view, through the screen, a second field of view different from the first field of view.

15 Claims, 5 Drawing Sheets

(56) References Cited

U.S. PATENT DOCUMENTS

| | | |
|---|---|---|
| 2014/0121669 A1 | 5/2014 | Claus |
| 2015/0077528 A1* | 3/2015 | Awdeh .................. A61B 3/005 348/78 |
| 2018/0168741 A1 | 6/2018 | Swayze et al. |
| 2020/0107002 A1 | 4/2020 | Casas |
| 2021/0196384 A1* | 7/2021 | Shelton, IV ........... A61B 34/10 |

FOREIGN PATENT DOCUMENTS

| | | |
|---|---|---|
| WO | 2015126466 A1 | 8/2015 |
| WO | 2020058808 A1 | 3/2020 |

\* cited by examiner

PRESENTING VISUAL AND THERMAL IMAGES IN A HEADSET DURING PHACOEMULSIFICATION

FIELD OF THE INVENTION

The present invention relates generally to medical imaging, and specifically to presenting, in a headset, visual and/or thermal images of an eye during a phacoemulsification procedure.

BACKGROUND OF THE INVENTION

Because of the delicate nature of some eye surgeries such as phacoemulsification, ophthalmic surgeons can use magnification devices such as microscopes for visualization and magnification of a surgical site. However, surgery using a microscope can pose some challenges for the surgeon, because the surgical site can be viewed only when the surgeon's eyes are directly aligned with the microscope's eyepieces. Therefore, if a surgeon wants to check settings or surgical parameters of the surgical system, the surgeon may need to pause the surgery, change his or her gaze from the surgical site to a surgical console that shows the settings, and then turn back to the surgical site. While this may take only a few seconds each time, the multiple pauses may decrease the efficiency of the surgery.

In addition, the surgeon may be required to hold his or her head at an awkward angle in order to look through the microscope. Over time, fatigue may make this position uncomfortable.

U.S. Patent Application 2014/0121669 to Claus describes a method for controlling a phacoemulsification system based on real-time analysis of image data. In some embodiments, the method includes detecting surgical events from image data collected by a surgical microscope focused on an ocular surgical procedure, establishing a desired response for each detected surgical event, delivering the desired response to the ocular surgical instrument as a set of software instructions, and altering the surgical procedure based on the desired response received as the set of software instructions.

U.S. Patent Application 2012/0022546 to Hubschman et al., describes a method for providing a surgeon with guidance concerning a distance separating a working end of a phacoemulsification instrument and the posterior portion of the capsule of the eye during surgical procedures. In some embodiments, the method includes visual and/or auditory conveyance of distance information to the surgeon wherein visual information may be conveyed by overlaying it with real visual images of actual surface features viewed by the surgeon.

U.S. Patent Application 2018/0168741 to Swayze et al., describes a surgical system with an augmented reality display. In some embodiments, the system includes a detector that comprises an array of pixels configured to detect light reflected by a surgical device and generate a first signal that includes an image of the surgical device. The surgical system may also include a processor configured to receive the first signal and a second signal representative of one or more operating parameters of the surgical device, and to generate a modified image of the surgical device that includes information related to one or more operating parameters.

The description above is presented as a general overview of related art in this field and should not be construed as an admission that any of the information it contains constitutes prior art against the present patent application.

SUMMARY OF THE INVENTION

There is provided, in accordance with an embodiment of the present invention, a surgical imaging system, including a first imaging device configured to generate a real-time visual image of a first field of view of a patient, a second imaging device configured to generate a real-time thermal image of the first field of view, a retaining structure, configured to be positioned in proximity to an eye of an operator of the system, a semi-transparent screen configured to be mounted on the structure in front of the eye of the operator, and a processor configured to receive the real-time visual and thermal images from the imaging devices, and upon receiving an indication from the operator, to present, on the semi-transparent screen, the real-time visual image, the real-time thermal image or the real-time thermal image overlaid on the real-time visual image, focused to a point in proximity to a near point of the eye of the operator while the operator is capable of viewing through the semi-transparent screen a second field of view different from the first field of view.

In some embodiments, the surgical imaging system is configured to present the real-time image, the real-time thermal image or the real-time thermal image overlaid on the real-time visual image by toggling, on the semi-transparent screen, the presentation of the real-time image, the real-time thermal image and the real-time thermal image overlaid on the real-time visual image in a round-robin fashion In additional embodiments, the first field of view of the patient includes one or more surgical tools used to perform a surgical procedure on the patient.

In one embodiment, the first field of view includes an eye of the patient, and the surgical tools are used to perform the surgical procedure on the eye of the patient.

In another embodiment, the surgical procedure includes phacoemulsification.

In an additional embodiment, the thermal image includes temperature information for tissue in the eye of the patient and the one or more surgical tools.

In a supplemental embodiment, the processor is further configured to present, on the semi-transparent screen, information about the surgical procedure.

There is also provided, in accordance with an embodiment of the present invention, a method for viewing a surgical procedure, including receiving a real-time visual image from a first imaging device having a first field of view of a patient, receiving a real-time thermal image from a second imaging device having the first field of view, and upon receiving an indication from an operator, presenting, by a processor on a semi-transparent screen, the real-time visual image, the real-time thermal image or the real-time thermal image overlaid on the real-time visual image, focused to a point in proximity to a near point of the eye of the operator while the operator is capable of viewing through the semi-transparent screen a second field of view different from the first field of view, wherein the semi-transparent screen is in front of an eye of an operator of the system and is mounted on a retaining structure positioned in proximity to the eye of the operator.

There is additionally provided, in accordance with an embodiment of the present invention, a computer software product including a non-transitory computer-readable medium, in which program instructions are stored, which instructions, when read by a computer, cause the computer to receive a real-time visual image from a first imaging device having a first field of view of a patient, to receive a real-time thermal image from a second imaging device having the first field of view, and to present, on a semi-transparent screen upon receiving an indication from an operator, the real-time visual image, the real-time thermal image or the real-time thermal image overlaid on the real-time visual image, focused to a point in proximity to a near point of the eye of the operator while the operator is capable of viewing through the semi-transparent screen a second field of view different from the first field of view, wherein the semi-transparent screen is in front of an eye of an operator of the system and mounted on a retaining structure positioned in proximity to the eye of the operator.

BRIEF DESCRIPTION OF THE DRAWINGS

The disclosure is herein described, by way of example only, with reference to the accompanying drawings, wherein.

DETAILED DESCRIPTION OF EMBODIMENTS

Overview

In a phacoemulsification procedure for an eye with a cataract, a surgeon positions a phacoemulsification tool so that a needle at the distal end of the tool engages a lens of the eye. Upon engaging the lens, the surgeon can instruct the tool to deliver ultrasonic energy to the needle so as to emulsify the lens. While emulsifying the lens, the handle may heat up as a result of the ultrasonic energy generated in the handle. The heat generation may be minimized by maintaining elements of the probe in resonance, but this is no easy matter because of the numerous and variable resonances (mechanical and electrical) of the probe. In addition, the eye is extremely sensitive to heat, and should not be raised to a temperature greater than 42° C. Thus, during a phacoemulsification procedure, even when probe elements are generating minimum heat, it is important to monitor temperature of the eye tissue.

Embodiments of the present invention provide a method and a system for presenting, to a headset worn by a surgeon, visual (i.e., visible spectrum) and thermal images of a phacoemulsification procedure. As explained hereinbelow, the system may comprise a first imaging device configured to generate a real-time visual image of a first field of view of a patient, and a second imaging device configured to generate a real-time thermal image of the first field of view. The first field of view is typically defined by optics of the first and the second imaging devices.

The headset may also comprise a retaining structure, configured to be positioned in proximity to an eye of an operator of the system, and a semi-transparent screen configured to be mounted on the structure in front of the eye of the operator. When looking through the semi-transparent screen, the operator has a second field of view that is typically defined by the retaining structure, in a manner similar to the field of view of an eyeglasses wearer being defined by the frame of the eyeglasses.

The system may additionally comprise a processor configured to receive the real-time visual and thermal images from the imaging devices. Upon receiving an indication from an operator, the processor can be configured to present, on the semi-transparent screen, the real-time visual image, the real-time thermal image or the thermal image overlaid on the visual image.

In embodiments of the present invention, the image (i.e., the real-time visual image, the real-time thermal image or the thermal image overlaid on the visual image) presented on the semi-transparent screen can be focused to a point in proximity to a near point of the eye of the operator while the operator is capable of viewing through the semi-transparent screen the second field of view different from the first field of view. In embodiments described herein, the near point of the eye indicates the closest point (typically around 25 centimeters) at which an object can be placed and so as to form a focused image on the retina.

During a phacoemulsification procedure, systems implementing embodiments of the present invention can present, to the surgeon on the semi-transparent screen, the visual or thermal images of the eye being treated when the surgeon's eye is focused on a point in proximity to the near point of the eye. However, if the surgeon is focused on the patient (i.e., at a point that is typically not in proximity to the near point of the eye) the surgeon can view the patient in the second field of view, by "looking through" the semi-transparent screen.

In additional embodiments, the system can present, to the surgeon on the semi-transparent screen, guidance, and other information on the procedure in progress.

System Description

Figure 1:
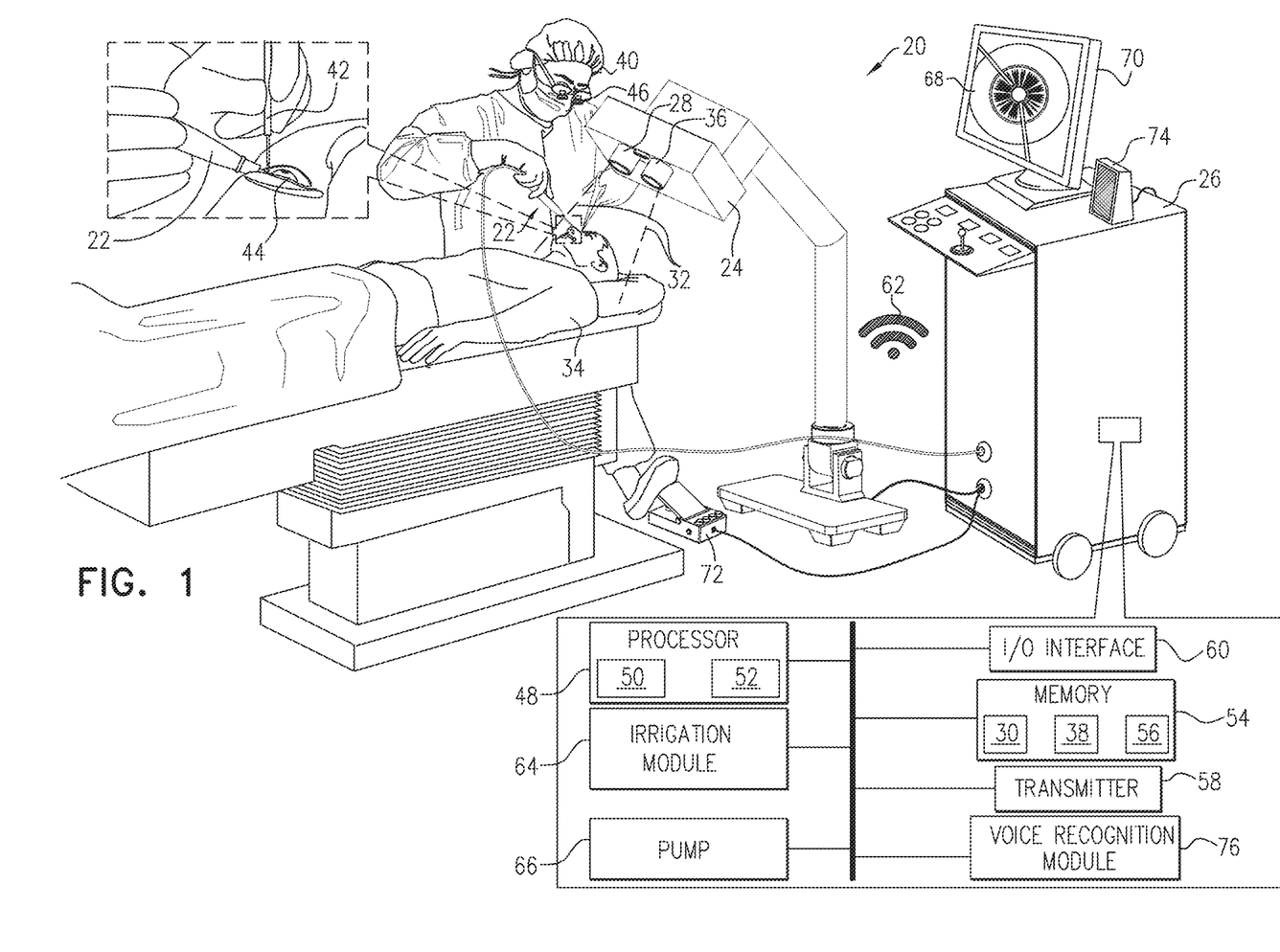
FIG. 1 is a schematic pictorial illustration of a medical system 20 comprising a visible spectrum camera and a thermal camera that capture real-time images of an eye during a phacoemulsification procedure, in accordance with an embodiment of the present invention.

FIG. 1 is a schematic pictorial illustration of a medical system 20 configured to be used when performing a phacoemulsification procedure, in accordance with an embodiment of the present invention. In the example shown in FIG. 1, medical system 20 comprises a phacoemulsification probe 22 and a medical imaging system 24 that are both coupled to a control console 26. Phacoemulsification probe 22 is described in the description referencing FIG. 2 hereinbelow.

Medical imaging system 24 comprises a visible spectrum camera 28 that is configured to capture and generate a real-time visible spectrum image 30 (FIG. 4), also referred to herein as visual image 30, of a field of view 32 comprising a patient 34, and a thermal camera 36 that is configured to capture and generate a real-time thermal image 38 (i.e., an image in the far infra-red) of field of view 32 comprising the patient. In embodiments herein, cameras 28 and 36 may also be referred to as imaging devices 28 and 36.

As described supra, field of view 32 (also referred to herein as a first field of view) is typically governed by optics of visible spectrum camera 28 and thermal camera 36. While the configuration in FIG. 1 shows a single field of view 32 for cameras 28 and 36, cameras having different fields of view, but with a common sub-field of view that comprises patient 34, are considered to be within the spirit and scope of the present invention.

A medical professional 40 (also referred to herein as an operator) typically uses surgical tools such as phacoemulsification probe 22 and a secondary instrument 42 to perform a phacoemulsification procedure on an eye 44 of patient 34. In embodiments described herein, medical professional 40 can wear a headset 46 that presents visual image 30 and/or real-time thermal image 38 (FIG. 5) to the medical professional 40. In some embodiments, headset 46 can receive the images in wireless signals received from console 26. Headset 46 is described in the description referencing FIG. 3 hereinbelow.

Control console 26 may also comprise a processor 48. Processor 48 may comprise real-time noise reduction circuitry 50 typically configured as a field programmable gate array (FPGA), followed by an analog-to-digital (A/D) signal conversion integrated circuit 52. The processor can pass the signal from A/D circuit 52 to another processor and/or can be programmed to perform one or more algorithms disclosed herein, each of the one or more algorithms comprising steps described hereinbelow. The processor uses circuitry 50 and circuit 52, as well as features of modules which are described in more detail below, in order to perform the one or more algorithms.

Control console 26 may additionally comprise a memory 54 that is configured to store images 30 and 38. As described hereinbelow, processor 48 can generate, and store to memory 54, a real-time image 56 that comprises visual image 30 and/or thermal image 38, as well as procedure information that can be useful to medical professional 40 performing a phacoemulsification procedure. Memory 54 may comprise any suitable volatile and/or non-volatile memory, such as random-access memory or a hard disk drive.

In the configuration shown in FIG. 1, console 26 also comprises a wireless transmitter 58 and an input/output (I/O) communications interface 60. Wireless transmitter 58 can be configured to transmit wireless signals 62 comprising real-time image 56 to headset 46. I/O interface 60 enables control console 26 to transfer images 30 and 38 from cameras 28 and 36 to memory 54, and to transfer real-time image 56 from the memory to wireless transmitter 58.

Console 26 may also comprise an irrigation module 64, and a pump 66. Irrigation module 64 is configured to deliver an irrigation fluid (e.g., a saline solution) to phacoemulsification probe 22 at a controllable rate. The operation of pump 66 is described in the description referencing FIG. 2 hereinbelow.

During a phacoemulsification procedure, processor 48 can present information 68 (e.g., images 30, 38 or 56) about the procedure to medical professional 40 on a display 70. In some embodiments, medical system 20 may comprise a physical input device, such as a pedal 72, that medical professional 40 may use to control the presentation of images 30 and 38 on headset 46, as described hereinbelow.

In the configuration shown in FIG. 1, medical console 26 also comprises a voice capture device 74 (e.g., a microphone) and a voice recognition module 76. In some embodiments, voice capture device 74 can capture a vocal input from medical professional 40, and convey the vocal input to voice recognition module 76. Voice recognition module 76 can translate the received vocal input into instructions that processor 48 can process so as to control the presentation of images 30 and/or 38 on headset 46.

Figure 2:
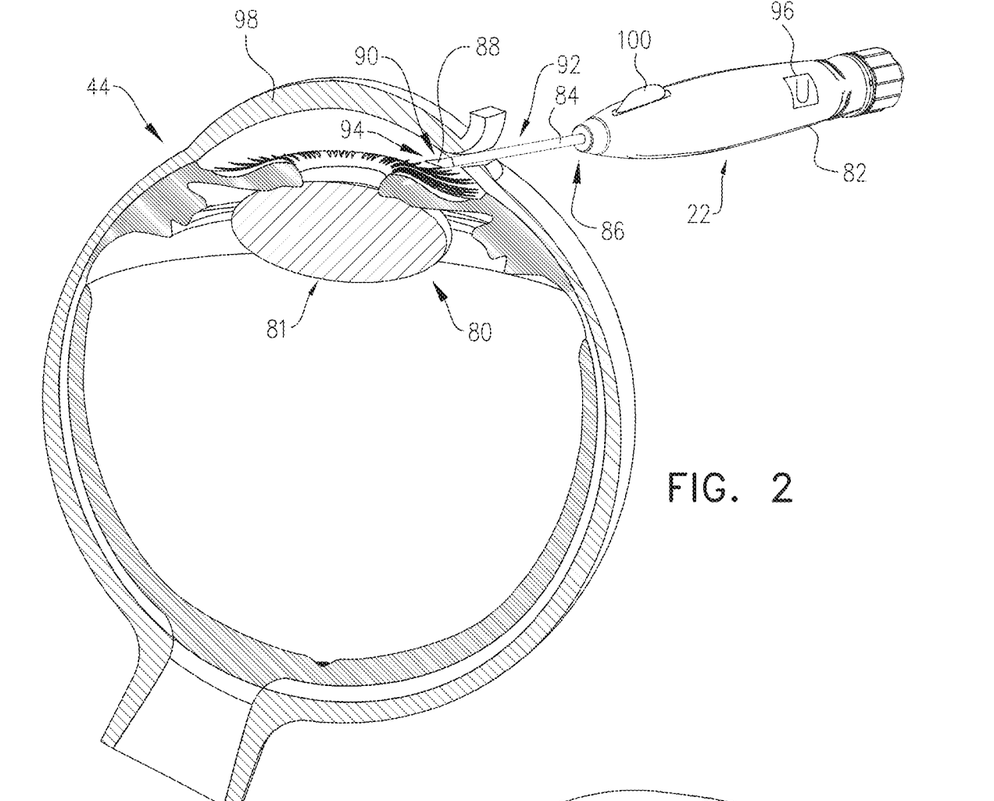
FIG. 2 is a schematic pictorial illustration of a phacoemulsification probe performing a phacoemulsification procedure, in accordance with an embodiment of the present invention.

FIG. 2 is a schematic pictorial illustration of phacoemulsification probe 22 performing a phacoemulsification procedure on a cataract 80 in a lens 81 of eye 44, in accordance with an embodiment of the present invention. Phacoemulsification probe 22 comprises a handle 82 comprising a shaft 84 that extends from a distal end 86 of the handle, and a needle 88 that extends from a distal end 90 of the shaft. In some embodiments, shaft 84 may also comprise an irrigation lumen 92 that can deliver irrigation fluid from irrigation module 64 to eye 44, and needle 88 may comprise an aspiration lumen 94 through which pump 66 can aspirate particles from the eye.

Phacoemulsification probe 22 may also comprise an ultrasonic transducer 96. In the example shown in FIG. 2, medical professional 40 manipulates handle 82 so as insert needle 88 through a cornea 98 of eye 44 so as to treat cataract 80. In response to medical professional 40 pressing a button 100 on handle (or in an alternate embodiment, a foot pedal may be used), ultrasonic transducer 96 generates vibration energy which it transfers to needle 88, and the vibration energy from the needle sculpt and emulsify lens 81. During the procedure, vibrating needle 88 can break up lens 81 into multiple pieces, and each of the pieces is emulsified and aspirated out by suction pump 66 via lumen 94.

Figure 3:
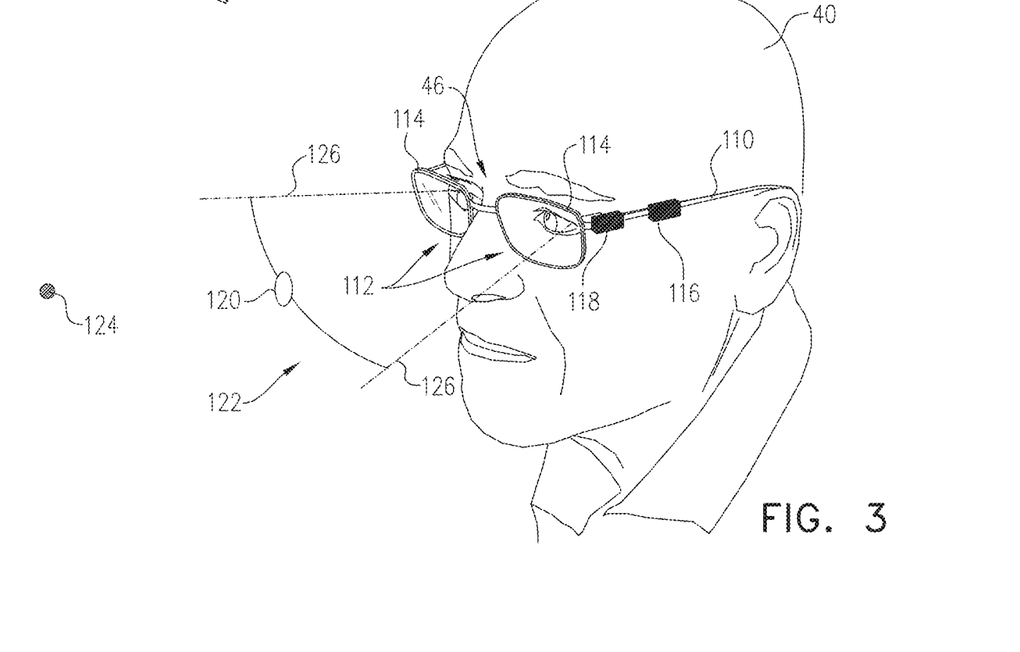
FIG. 3 is a schematic pictorial illustration of a headset that can be worn by a surgeon, and is configured to present, to the surgeon, the real time images captured by the visible spectrum and thermal cameras, in accordance with an embodiment of the present invention.

FIG. 3 is a schematic pictorial illustration of medical professional 40 wearing headset 46, in accordance with an embodiment of the present invention. Headset 46 comprises a retaining structure 110 that is configured to be positioned in proximity to left and right eyes 112 of medical professional 40, and substantially similar semi-transparent screens 114 that are configured to be mounted respectively on the retaining structure in front of eyes 112.

In the configuration shown in FIG. 3, headset 46 also comprises a wireless receiver 116 that is configured to receive wireless signals 62 comprising real-time image 56, and an image projector 118 that is configured to present, on screens 114, the received real-time image, as described hereinbelow. In some embodiments, image projector 118 can be configured to present, on semi-transparent screens 114, real-time image 56 focused to a point 120 in proximity to a near point 122 of eyes 112. Near point 122 is approximately 25 centimeters from each given eye 112, and references the closest point at which an object can be placed in front of the given eye so as to form a focused image on the eye's retina, (i.e., within the eye's accommodation range).

In other words, if eyes 112 are focused on point 120, then eyes 112 will "see" real-time image 56. However, if eyes 112 are focused on a point 124 that is beyond near point 122, then eyes 112 will see point 124 "through" semi-transparent screens 114. When eyes 112 see point 124 "through" semi-transparent screens 114, eyes 112 have a field of view 126 (also referred to herein as a second field of view), defined by retaining structure 110, that is different than field of view 32.

Therefore, during a surgical procedure such as phacoemulsification, medical professional 40 can see patient 34 in field of view 126 if eyes 112 are focused on point 124 (e.g., on the patient), and can view the patient in field of view 32 if eyes 112 are focused on point 120.

Figure 4:
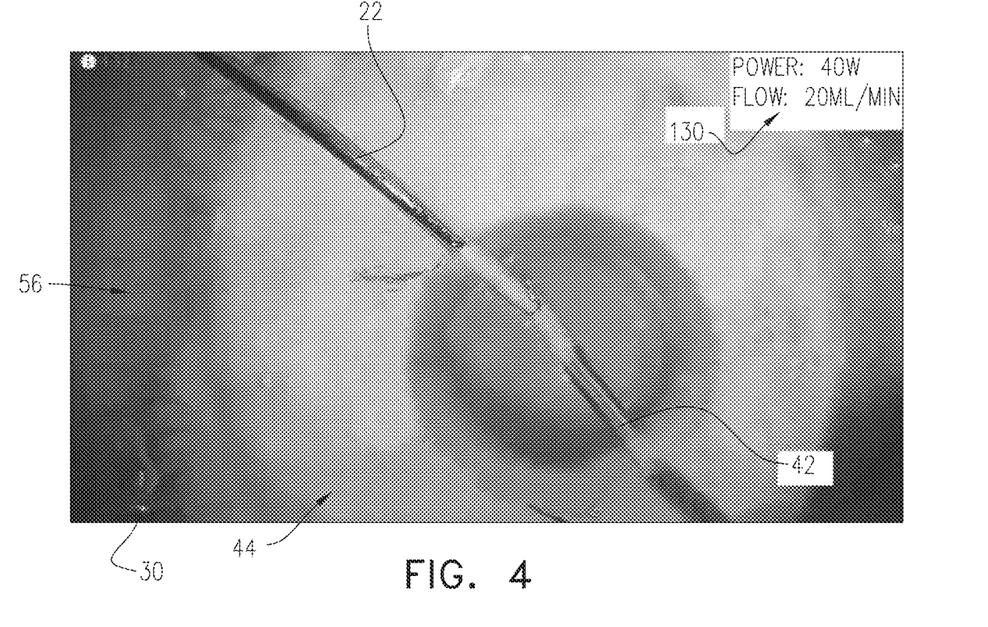
FIG. 4 is a schematic pictorial illustration of a real-time visible spectrum image of an eye during a phacoemulsification procedure that is captured by the visible spectrum camera, in accordance with an embodiment of the present invention.

FIG. 4 is a schematic pictorial illustration of real-time image 56 comprising visual image 30 of eye 44 and surgical tools such as probe 22 and secondary instrument 42 during a phacoemulsification procedure, in accordance with an embodiment of the present invention. In some embodiments, processor 48 can generate real-time image 56 by overlaying, on visual image 30, procedure information 130. Examples of information 130 that processor 48 can overlay on real-time image 30 include, but are not limited to, a stroboscopic video showing movement of needle 88, current power applied to ultrasonic transducer 96 and pump flow for irrigation module 64.

Figure 5:
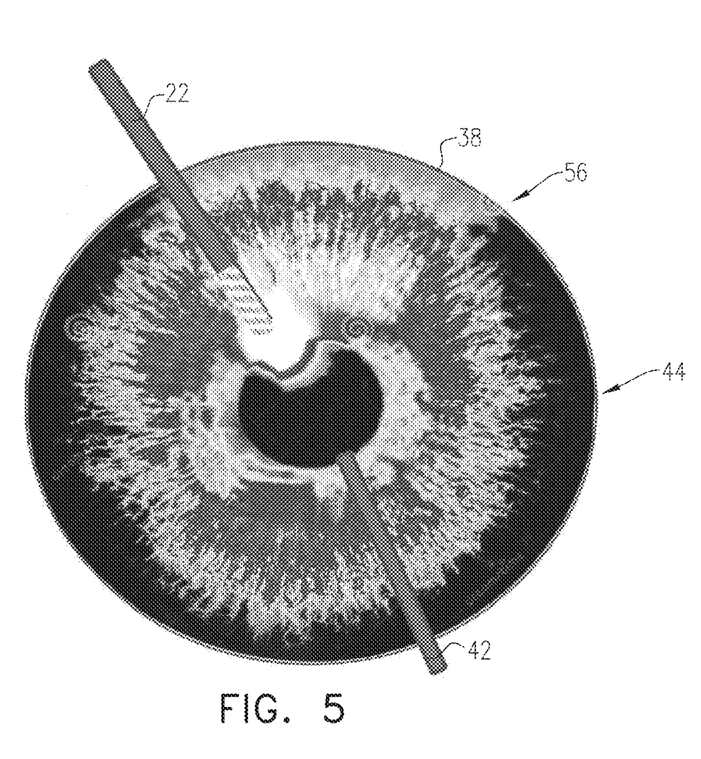
FIG. 5 is a schematic pictorial illustration of a real-time thermal image of an eye during the phacoemulsification procedure that is captured by the thermal camera, in accordance with an embodiment of the present invention.

FIG. 5 is a schematic pictorial illustration of real-time image 56 comprising real-time thermal image 38 of eye 44 and surgical tools such as probe 22 and secondary instrument 42 during a phacoemulsification procedure, in accordance with an embodiment of the present invention. FIG. 5 illustrates real-time image 56 in gray scale, but it will be understood that typically the image is a color image, with different colors representing different temperatures. Thermal image 38 conveys temperature information for tissue in eye 44 and surgical instruments 22 and 42.

Figure 6:
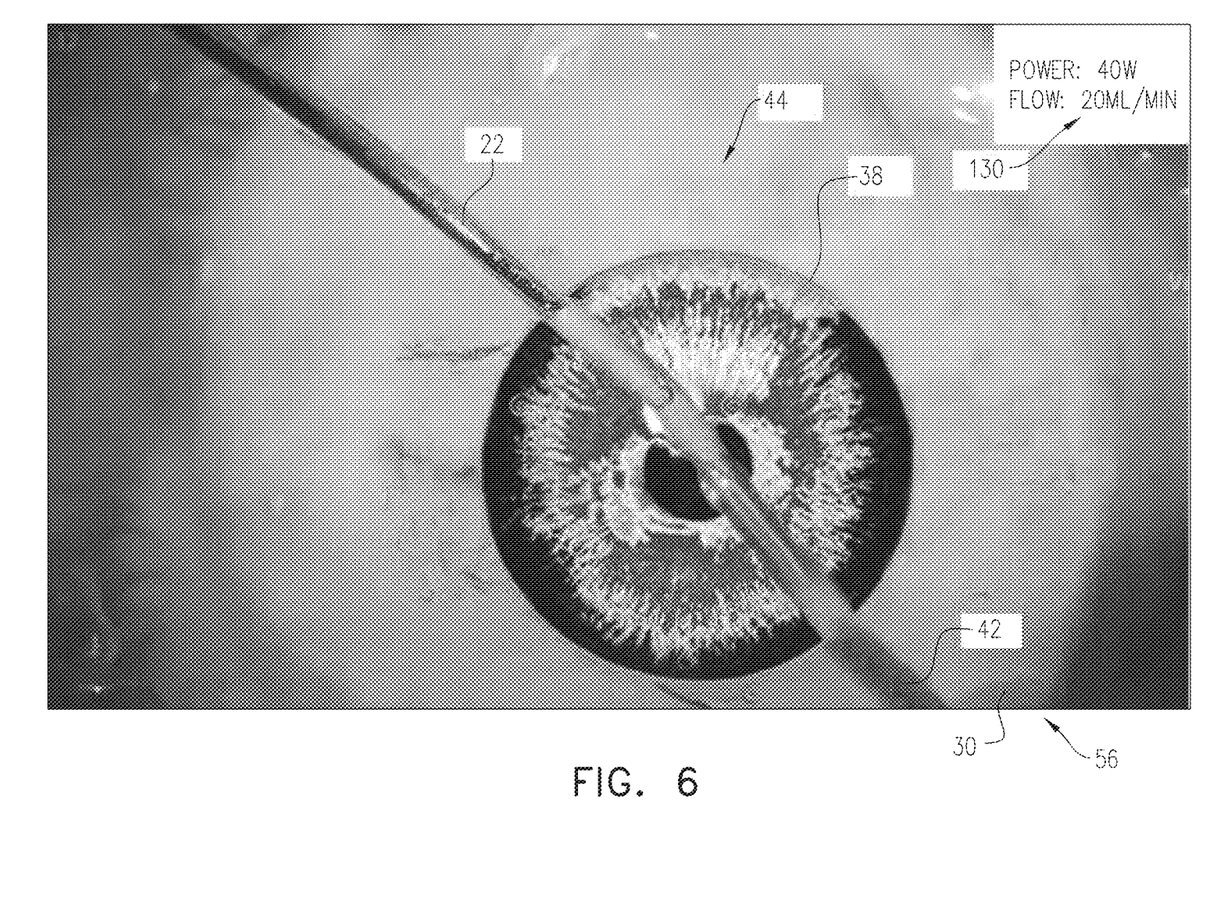
FIG. 6 is a schematic pictorial illustration of the real-time thermal image overlaid on the real-time visible spectrum image, in accordance with an embodiment of the present invention.

FIG. 6 is a schematic pictorial illustration of real-time image 56 comprising real-time thermal image 38 overlaid on visual image 30 during a phacoemulsification procedure, in accordance with an embodiment of the present invention. In some embodiments, processor 48 can generate real-time image 56 by overlaying, on images 30 and 38, procedure information 130.

Real-Time Visual and/or Thermal Image Presentation

Figure 7:
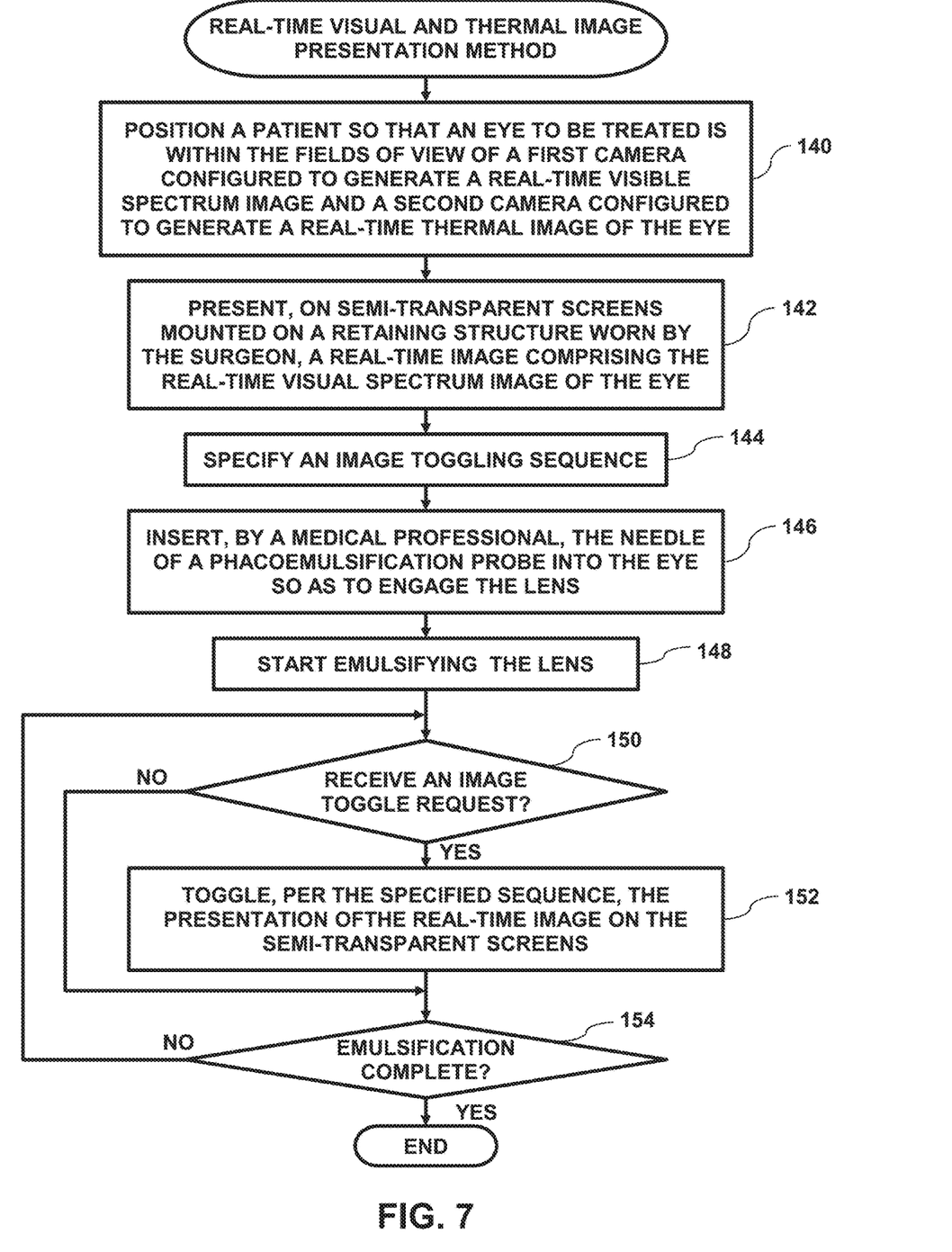
FIG. 7 is a flow diagram that schematically illustrates a method of presenting the real-time images in the headset worn by the surgeon during a phacoemulsification procedure, in accordance with an embodiment of the present invention.

FIG. 7 is a flow diagram that schematically illustrates a method of presenting, on semi-transparent screens 114, real-time image 56 of a phacoemulsification procedure, in accordance with an embodiment of the present invention. In a positioning step 140, medical professional 40 positions patient 34 so that eye 44 (i.e., the eye to be treated) is within field of view 32.

In a first presentation step 142, processor 48 presents real-time visual spectrum image 30 on semi-transparent screens 114. To present real-time visual spectrum image 30 on semi-transparent screens 114, processor 48 can receive the real-time visual spectrum image 30 from camera 28, generate real-time image 56 from the received image, and transmit, via transmitter 58, the generated real-time image 56 in wireless signal 62. Upon wireless receiver receiving wireless signal 62, image projector 118 can present real-time image 56 on semi-transparent screens 114. In embodiments of the present invention, image projector 118 presents real-time image 56 on semi-transparent screens 114 focused to point 120 in proximity to near point 122.

In a specification step 144, processor 48 specifies an image toggling sequence for content to present in real-time image 56 on semi-transparent screens 114. For example, processor 48 can specify the sequence as follows:
 A. Real-time visual spectrum image 30 (also referred to herein as image A in the sequence).
 B. Real-time thermal image 38 (also referred to herein as image B in the sequence).
 C. Real-time thermal image 38 overlaid on real-time visual spectrum image 30 (also referred to herein as image C in the sequence).

In this example, processor 48 can toggle between images A, B and C in a round-robin fashion.

Presenting real-time visual spectrum image 30 (i.e., image A in the sequence) is described in the description referencing step 142 hereinabove. To present real-time thermal image 38 (i.e., image B in the sequence), processor 48 can receive the real-time thermal image 38 from camera 36, generate real-time image 56 from the received image, and transmit, via transmitter 58, the generated real-time image 56 in wireless signal 62. Upon wireless receiver receiving wireless signal 62, image projector 118 can present real-time image 56 on semi-transparent screens 114.

To present real-time thermal image 38 overlaid on real-time visual spectrum image 30 (i.e., image C in the sequence), processor 48 can receive the real-time visual spectrum image 30 from camera 28, receive the real-time thermal image 38 from camera 36, register the received thermal image 38 to the received visual image 30, generate real-time image 56 by overlaying the received thermal image 38 on the received visual image 30, and transmit, via transmitter 58, the generated real-time image 56 in wireless signal 62. Upon wireless receiver receiving wireless signal 62, image projector 118 can present real-time image 56 on semi-transparent screens 114.

Typically, thermal camera 36 is registered to visual spectrum image camera 30 (or vice versa) prior to the phacoemulsification procedure, using techniques known in the art. For example, an individual (e.g., medical professional 40) can place a heated chessboard at point 124, and perform the registration by aligning, on display 70, the thermal and the visual spectrum images of the chessboard.

In an insertion step 146, medical professional inserts needle into eye 44, and manipulates handle 82 so that the needle engages lens 81 in eye 44.

In an emulsification step 148, medical professional 40 starts the phacoemulsification procedure to emulsify lens 81. To emulsify lens 81, medical professional 40 presses button 100 (or in an alternate embodiment a foot pedal), and in response to the pressed button, ultrasonic transducer conveys ultrasonic energy to needle 88. The ultrasonic energy causes the needle to vibrate and emulsify tissue of lens 81 in proximity to needle 88.

In a first decision step 150, processor 48 checks if there is an image toggle request from medical professional 40. In the configuration shown in FIG. 1, medical professional 40 can send the image toggle request by pressing on pedal 72 or a button located on pedal 72.

If processor 48 receives an input toggle request, then, in step 152, processor 48, toggles the presentation of real-time image 56 on semi-transparent screens 114 per the image toggling sequence described supra.

Finally, in a second decision step 154, if the emulsification of lens 81 is not complete, then the method returns to step 150. The method ends when the emulsification of lens 81 is completed or when indicated by medical professional 40.

Returning to step 150, if processor 48 does not receive an image toggle request, then the method continues with step 154.

While the embodiments in steps 150-152 describe toggling the content in real-time image 56 in response to an image toggle request, other methods of changing the content in real-time image 56 are considered to be within the spirit and scope of the present invention. For example, medical system 20 may comprise first, second and third physical input devices, herein, by way of example, assumed to comprise additional pedals 72 or additional buttons 100. In this case, in response to an input from the first input device, processor 48 generates real-time image 56 comprising real-time visual spectrum image 30, in response to an input from the second input device, processor 48 generates real-time image 56 comprising real-time thermal image 38, and in response to an input from the third input device, processor 48 generates real-time image 56 comprising real-time thermal image 38 overlaid on real-time visual spectrum image 30. In an additional embodiment, processor 48 can use signals from voice recognition module 76 to toggle or select the content in real-time image 56 based on vocal inputs from medical professional 40.

It will be appreciated that the embodiments described above are cited by way of example, and that the present invention is not limited to what has been particularly shown and described hereinabove. Rather, the scope of the present invention includes both combinations and subcombinations of the various features described hereinabove, as well as variations and modifications thereof which would occur to persons skilled in the art upon reading the foregoing description and which are not disclosed in the prior art.

The invention claimed is:

1. A surgical imaging system, comprising:
 a first imaging device configured to generate a real-time visual image of a first field of view of a patient;
 a second imaging device configured to generate a real-time thermal image of the first field of view;
 a retaining structure having one or more lenses, the retaining structure configured to be positioned in proximity to an eye of an operator of the system;
 a semi-transparent screen configured to be mounted on the retaining structure in front of the eye of the operator;
 an image projector configured to present on the semi-transparent screen; and
 a processor configured to receive the real-time visual and thermal images from the imaging devices, and upon receiving an indication from the operator, cause the image projector to present, on the semi-transparent screen, the real-time visual image, the real-time thermal image or the real-time thermal image overlaid on the real-time visual image, focused to a point in proximity to a near point of approximately 25 centimeters of the eye of the operator looking at the semi-transparent screen while, without turning off presented images, the operator is capable of viewing through the same semi-transparent screen a second field of view of the patient defined by the one or more lenses of the retaining structure, wherein the second field of view is different from the first field of view, and has a focus point substantially beyond the point of focus seeing the real-time visual image displayed on the transparent screen.

2. The surgical imaging system according to claim 1, wherein the processor is configured to cause the image projector to present the real-time image, the real-time thermal image or the real-time thermal image overlaid on the real-time visual image by toggling, on the semi-transparent screen, the presentation of the real-time image, the real-time thermal image and the real-time thermal image overlaid on the real-time visual image in a round-robin fashion.

3. The surgical system according to claim 1, wherein the first field of view of the patient comprises one or more surgical tools used to perform a surgical procedure on the patient.

4. The surgical system according to claim 3, wherein the first field of view comprises an eye of the patient, and wherein the surgical tools are used to perform the surgical procedure on the eye of the patient.

5. The surgical system according to claim 3, wherein the surgical procedure comprises phacoemulsification.

6. The surgical system according to claim 5, wherein the thermal image comprises temperature information for tissue in the eye of the patient and the one or more surgical tools.

7. The surgical system according to claim 3, wherein the processor is further configured to cause the image projector to present, on the semi-transparent screen, information about the surgical procedure.

8. A method for viewing a surgical procedure, comprising:
 receiving a real-time visual image from a first imaging device having a first field of view of a patient;
 receiving a real-time thermal image from a second imaging device having the first field of view; and
 upon receiving an indication from an operator, presenting, by a processor causing an image projector to project on a semi-transparent screen mounted on a retaining structure positioned in proximity to an eye of an operator, the real-time visual image, the real-time thermal image or the real-time thermal image overlaid on the real-time visual image, focused to a point in proximity to a near point of approximately 25 centimeters of the eye of the operator looking at the semi-transparent screen while, without turning off presented images, the operator is capable of viewing through the same semi-transparent screen a second field of view of the patient defined by one or more lenses of the retaining structure, wherein the second field of view is different from the first field of view, and has a focus point substantially beyond the point of focus seeing the real-time visual image displayed on the semi-transparent screen.

9. The method according to claim 8, wherein presenting the real-time image, the real-time thermal image or the real-time thermal image overlaid on the real-time visual image comprises toggling, on the semi-transparent screen, the presentation of the real-time image, the real-time thermal image and the real-time thermal image overlaid on the real-time visual image in a round-robin fashion.

10. The method according to claim 8, wherein the first field of view of the patient comprises a view of one or more surgical tools used to perform the surgical procedure on the patient.

11. The method according to claim 10, wherein the first field of view comprises a view of an eye of the patient, and wherein the surgical tools are used to perform the surgical procedure on the eye of the patient.

12. The method according to claim 10, wherein the surgical procedure comprises phacoemulsification.

13. The method according to claim 12, wherein the thermal image comprises temperature information for tissue in the eye of the patient and the one or more surgical tools.

14. The method according to claim 10, further comprising presenting, by the processor causing the image projector to display on the semi-transparent screen, information about the surgical procedure.

15. A computer software product comprising a non-transitory computer-readable medium, in which program instructions are stored, which instructions, when read by a computer, cause the computer to:
 receive a real-time visual image from a first imaging device having a first field of view of a patient;
 receive a real-time thermal image from a second imaging device having the first field of view; and present, by an image projector on a semi-transparent screen upon receiving an indication from an operator, the real-time visual image, the real-time thermal image or the real-time thermal image overlaid on the real-time visual image, focused to a point in proximity to a near point of approximately 25 centimeters of an eye of the operator looking at the semi-transparent screen while, without turning off presented images, the operator is capable of viewing through the same semi-transparent screen a second field of view of the patient different from the first field of view, wherein the second field of view has a focus point substantially beyond the point of focus of the seeing images displayed on the semi-transparent screen, wherein the semi-transparent screen is in front of an eye of an operator of the system and mounted on a retaining structure positioned in proximity to the eye of the operator.

* * * * *